US00PP30910P3

(12) United States Plant Patent
O'Connell

(10) Patent No.: US PP30,910 P3
(45) Date of Patent: Sep. 24, 2019

(54) ***TACISEDUM* PLANT NAMED 'SOLAR FLARE'**

(50) Latin Name: *Tacisedum hybrida*
Varietal Denomination: SOLAR FLARE

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 17 days.

(21) Appl. No.: 15/732,287

(22) Filed: Oct. 18, 2017

(65) Prior Publication Data

US 2019/0116711 P1 Apr. 18, 2019

(51) Int. Cl.
*A01H 5/12* (2018.01)
*A01H 6/00* (2018.01)
*A01H 6/32* (2018.01)

(52) U.S. Cl.
USPC ..... Plt./479
CPC ..... *A01H 6/00* (2018.05); *A01H 5/12* (2013.01); *A01H 6/32* (2018.05)

(58) Field of Classification Search
USPC ..... Plt./479
See application file for complete search history.

*Primary Examiner* — Anne Marie Grunberg
(74) *Attorney, Agent, or Firm* — Cassandra Bright

(57) ABSTRACT

A new and distinct cultivar of *Tacisedum* plant named 'Solar Flare' is disclosed, characterized by attractive compact plant form with a distinctive star-shaped rosette morphology. Foliage has a distinctive copper-pink marginal color. The new cultivar produces offsets freely while maintaining a compact plant habit. Pink flowers are produced April through June in Southern California. *Tacisedum* is a useful genus, typically produced as container plants for the patio or as landscape plants, as a variety of ornamental purposes.

2 Drawing Sheets

Figure 1:
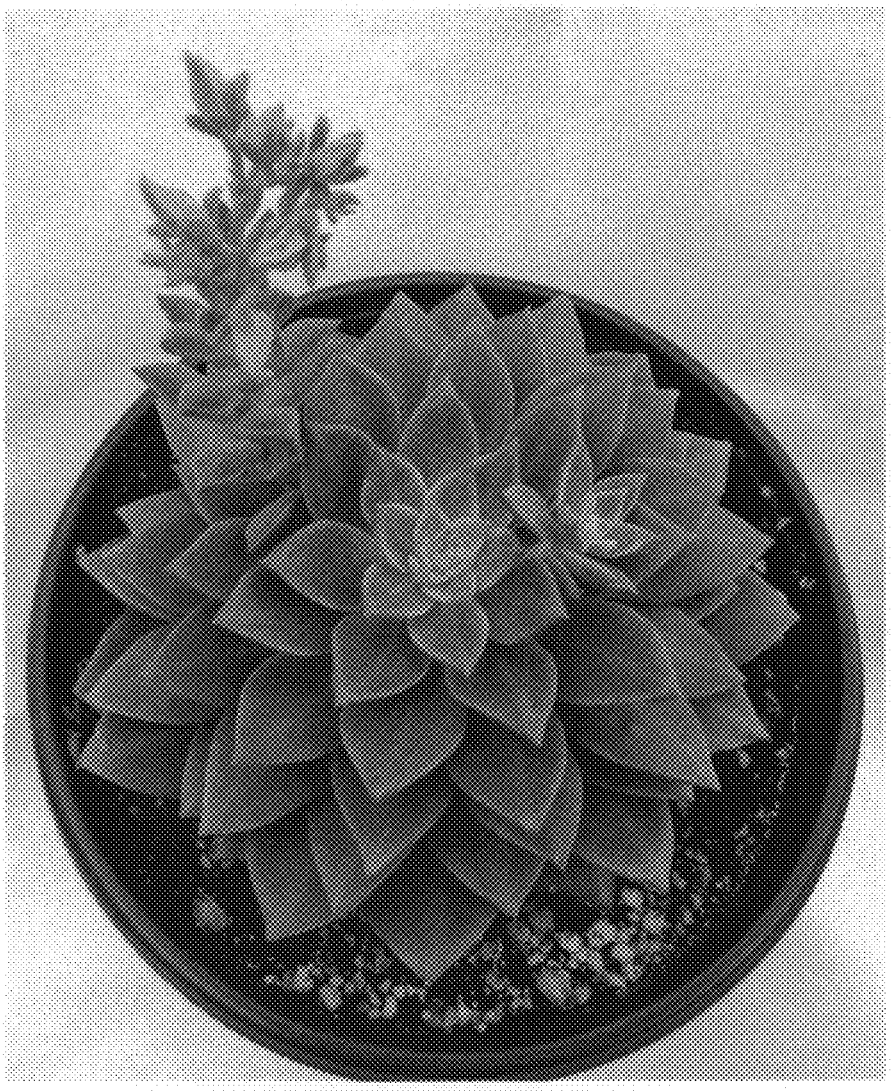

Latin name of the genus and species: *Tacisedum hybrida*.
Variety denomination: 'SOLAR FLARE'.

BACKGROUND OF THE INVENTION

The new cultivar, *Tacisedum* 'SOLAR FLARE', is the product of a planned breeding program. The new variety originated from a cross pollination of the proprietary, unpatented, seed parent, *Sedum hybrida* 'S06' with the pollen parent an unpatented, proprietary variety of *Tacitus bellum* referred to as 'Ruby 03'. The cross pollination was made during February 2014 in Vista, Calif., at a commercial greenhouse. The new cultivar 'SOLAR FLARE' was discovered by the inventor, Renee O'Connell, in March 2015, in Vista, Calif. at a commercial greenhouse.

Asexual reproduction of the new cultivar 'SOLAR FLARE' was first performed in Vista, Calif., at a commercial greenhouse, by terminal vegetative cuttings, *Tacisedum* 'SOLAR FLARE' has since produced multiple generations and has shown that the unique features of this cultivar are stable and reproduced true to type.

SUMMARY OF THE INVENTION

The cultivar 'SOLAR FLARE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SOLAR FLARE'. These characteristics in combination distinguish 'SOLAR FLARE' as a new and distinct *Tacisedum* cultivar:

1. *Tacisedum* 'Solar Flare' displays an unusual copper-pink leaf margin, a condition accentuated by bright light.
2. *Tacisedum* 'Solar Flare' offsets freely to produce an attractive, compact cluster.
3. *Tacisedum* 'Solar Flare' produces sprays of larger pink flowers April through June.
4. *Tacisedum* 'Solar Flare' exhibits a very concentric star shaped rosette, which in combination with the copper-pink leaf margin, produces an attractive geometric rosette.

PARENTAL COMPARISON

Plants of the new cultivar are similar to plants of the seed parent, in most horticultural characteristics, however, plants of the new cultivar differ in the following;

1. *Tacisedum* 'Solar Flare' exhibits a low-growing, concentric rosette, whereas the parent *Sedum* 'S06' is an upright, branching plant.
2. *Tacisedum* 'Solar Flare' produces larger pink flowers, while the parent *Sedum* 'S06' produces white flowers.
3. The flowers of the new cultivar *Tacisedum* 'Solar Flare' are produced April through June, whereas the flowers of the parent *Sedum* hybrid 'S06' are produced January through March.
4. The parent *Sedum* 'S06' grows with a somewhat lax morphology, while the new cultivar *Tacisedum* 'Solar Flare' exhibits a low-growing, concentric rosette morphology.
5. The parent *Sedum* 'S06' exhibits some orange coloring to the leaves, but without the copper-pink tinge that *Tacisedum* 'Solar Flare' displays.

Plants of the new cultivar are similar to plants of the pollen parent, in most horticultural characteristics, however, plants of the new cultivar differ in the following;

1. *Tacisedum* 'Solar Flare' produces pink flowers, whereas *Tacitus* 'Ruby 03' produces crimson flowers.
2. *Tacisedum* 'Solar Flare' produces green leaves with copper-pink margins, particularly in bright light, whereas the green leaves of the *Tacitus* 'Ruby 03' do not exhibit marginal color, even in brighter light.
3. *Tacisedum* 'Solar Flare' grows faster than *Tacitus* 'Ruby 03'.
4. The rosette of *Tacitus* 'Ruby 03' is approximately 7-9 cm in diameter; whereas *Tacisedum* 'Solar Flare' can produce rosettes of 12 cm diameter.

COMMERCIAL COMPARISON

Plants of the new cultivar are similar to plants of the commercial variety *Tacisedum* 'Spring Glow', U.S. Plant Pat. No. 29,463, in most horticultural characteristics, however, plants of the new cultivar differ in the following;

1. *Tacisedum* 'Spring Glow' forms mounded clusters to 6" in height and 8" or more in diameter, whereas *Tacisedum* 'Solar Flare' displays more geometric, low-growing clusters.
2. *Tacisedum* 'Spring Glow' produces clusters of lime green rosettes, blushed apically red in cooler weather, whereas *Tacisedum* 'Solar Flare' produces very concentric rosettes of olive green leaves with copper-pink margins.
3. *Tacisedum* 'Spring Glow' displays dense sprays of light pink flowers, whereas *Tacisedum* 'Solar Flare' produces sprays of darker pink flowers.
4. *Tacisedum* 'Solar Flare' has a shiny epidermis, whereas the epidermis of *Tacisedum* 'Spring Glow' is matte in appearance.
5. The leaves of *Tacisedum* 'Spring Glow' are very thickened, and have discernable internodal distances, as compared with the more flattened, appressed leaves of *Tacisedum* 'Solar Flare'.

The new cultivar 'Solar Flare' can be compared to the unpatented *Sedum adolphi*. Plants of *Sedum adolphi* are similar to plants of the new cultivar 'Solar Flare' in most horticultural characteristics. However, plants of the new cultivar 'Solar Flare' differ in the following:

1. *Sedum adolphi* produces lax, pendant stems, whereas *Tacisedum* 'Solar Flare' forms very concentric, low-growing rosettes.
2. *Tacisedum* 'Solar Flare' produces pink flowers whereas *Sedum adolphi* produces white flowers.
3. *Tacisedum* 'Solar Flare' produces olive green leaves with copper-pink margins, whereas *Sedum adolphi* produces yellow or yellow-orange leaves.
4. *Tacisedum* 'Solar Flare' flowers April through June, whereas *Sedum adolphi* flowers December to February.

BRIEF DESCRIPTION OF THE PHOTOGRAPHS

The accompanying photographs illustrate in full color typical of plants of *Tacisedum* 'Solar Flare' grown in a greenhouse in Vista, Calif. Age of the plant photographed is approximately 5 months from a terminal vegetative cutting. The photograph was taken using conventional techniques and although colors may appear different from actual colors due to light reflectance it is as accurate as possible by conventional photographic techniques. All photographs provided by the breeder.

FIG. 1 illustrates in full color *Tacisedum* 'Solar Flare' in a 1 gallon pot with a developing inflorescence.

Figure 2:
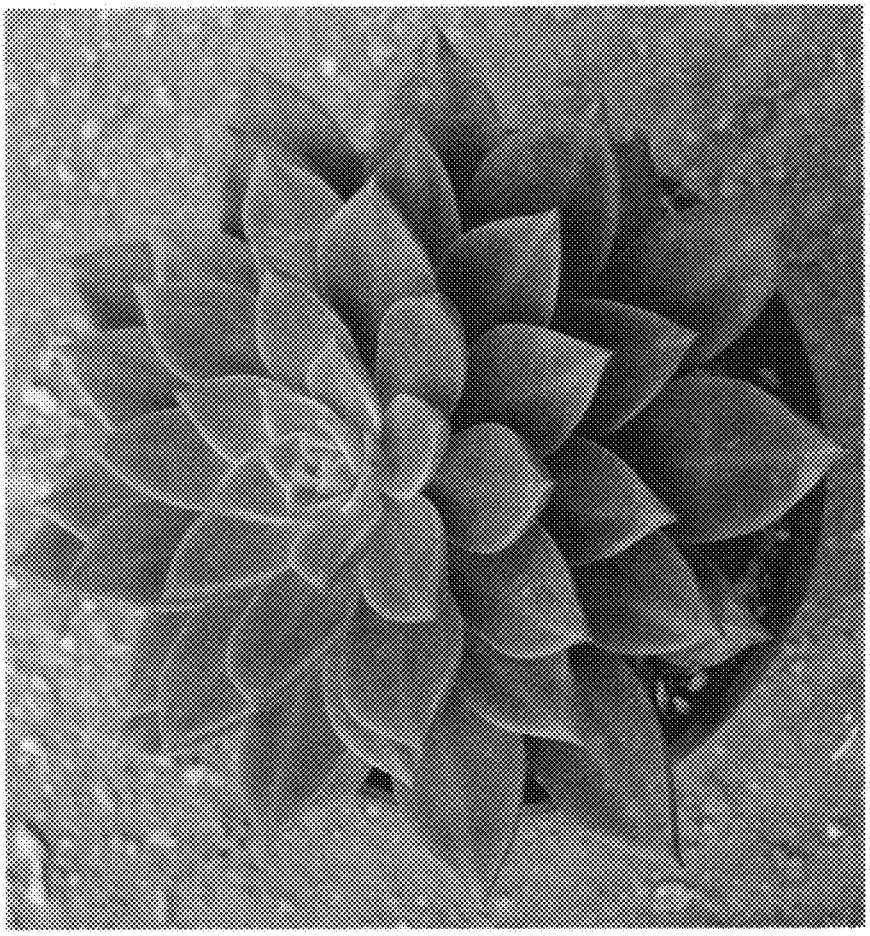

FIG. 2. illustrates in full color the plant morphology of *Tacisedum* 'Solar Flare'.

DETAILED BOTANICAL DESCRIPTION

In the following description, color references are made to The Royal Horticultural Society Colour Chart, except where general terms of ordinary dictionary significance are used. The following observations and measurements describe 'Solar Flare' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Tacisedum hybrida* 'SOLAR FLARE'.

PROPAGATION

Type of propagation typically used: Terminal vegetative cuttings.

Time to initiate roots: About 11 days at approximately 24° C.

Root description: Fibrous.

PLANT

Age of plant described: Approximately 4 months from a cutting.

Container size of the plant described: 1 gallon.

Growth habit: Somewhat flattened rosulate plant.

Height: Approximately 9 cm to top of highest leaf. Approximately 13 cm to top of highest inflorescence.

Plant spread: Approximately 15.0 cm.

Growth rate: Slow.

Branching characteristics: Moderately freely offsetting. Approximately 4 to 8 offsets on a plant of this size and age.

FOLIAGE

Leaf:

*Arrangement*.—Rosulate.

*Average length*.—5 to 6 cm.

*Average width*.—1.5 to 2.5 cm

*Width at base*.—Average: 7 mm.

*Thickness of leaf*.—Thickest section is in leaf center, near 6 mm.

*Shape of blade*.—Spatulate.

*Aspect*.—Slight upward cupping, oldest, lowest foliage nearly flat.

*Apex*.—Mucronate. Mucronation slightly sharp, approximately 2 to 3 mm, colored near Red 53A.

*Base*.—Broad attenuate.

*Margin*.—Entire.

*Texture of top surface*.—Glabrous.

*Texture of bottom surface*.—Glabrous.

*Appearance of top surface*.—Shiny.

*Appearance of bottom surface*.—Matte.

*Quantity of leaves per plant.*—Average range 80 to 100.

*Color.*—Young foliage upper side: Base near Yellow-Green 145D, mid-section near Green 138A. Upper margin Green 137A flushed Greyed-Purple N186A, with margin 187B. Young foliage under side: Base near Yellow-Green 145D, mid-section near Green 138A. Upper margin Green 137A flushed Greyed-Purple N186A, with margin 187B. Mature foliage upper side: Base near Yellow-Green 145D, mid-section near Green 138A. Upper margin Green 137A flushed Greyed-Purple N186A, with margin 187B. Mature foliage, under side: Base near Yellow-Green 145D, mid-section near Green 138A. Upper margin Green 137A flushed Greyed-Purple N186A, with margin 187B.

FLOWER

Natural flowering season: April through June.

Inflorescence type and habit: Erect, composed of simple or occasionally bifurcate cincinni, each cincinnus typically with 5 to 7 flowers and 3 to 5 buds.

Rate of flower opening: About 5 to 7 days from bud stage to open flower, depending on environmental conditions.

Flower longevity on plant: 6-10 days, depending upon ambient temperatures.

Quantity of flowers: About 5 to 7 individual flowers and 3 to 5 buds.

*Total inflorescence size.*—Height: Approximately 5 cm. Width: Approximately 8 cm.

*Corolla.*—Arrangement: Pentagonal, fused at base. Size: Length: Approximately 1.0 cm. Width: Approximately 2.2 cm at widest point. Lobe Length: Approximately 1.4 cm. Lobe width: Approximately 0.5 cm.

*Petals.*—Margin: Entire. Shape: Unfused section narrow deltate. Apex: Narrow acute. Base: Fused, approximately ¾ entire length. Texture: Glabrous, all surfaces. Length: Approximately 0.9 cm unfused, 0.7 cm fused. Width: Approximately 0.3 cm. Color: When opening: Outer surface: Near RHS Red 55A, streaked 55D. Inner surface: Near RHS Red 55A. Fully opened: Outer surface: Near RHS Red 55A, streaked 56D. Inner surface: Near RHS Red 55A, streaked 56D. Color Changes when Aging: Outer surface: Near RHS Red 56C streaked 55D, margin 55D. Inner surface: Near RHS Red 55B, streaks near 55B.

Bud (near opening):

*Shape.*—Conical.

*Length.*—Approximately 1.0 cm.

*Diameter.*—Approximately 0.8 cm.

*Color.*—Near Red 41C, flushed Yellow-Orange 19A.

Sepals:

*Length.*—3 to 5 mm.

*Width.*—2 to 5 mm.

*Margin.*—Entire.

*Shape.*—Irregular oblong.

*Apex.*—Acute.

*Base.*—Truncate.

*Texture.*—Glabrous, upper and lower surfaces.

*Appearance.*—Very slightly shiny, upper and lower surfaces.

*Color.*—Outer: Near Yellow-Green 146B, apex near Greyed-Purple 183A. Inner: Near Yellow-Green 146C.

Peduncle:

*Length.*—Average range 3 to 6 cm.

*Width.*—Approximately 5 mm.

*Strength.*—Strong.

*Texture.*—Glabrous.

*Color.*—Base near RHS Greyed-Orange 174D.

Pedicels:

*Length.*—Approximately 0.5 to 1.1 cm.

*Width.*—Approximately 0.2 cm.

*Strength.*—Strong, flexible.

*Texture.*—Glabrous.

*Color.*—Near RHS Greyed-Red 180C.

*Fragrance.*—None detected.

REPRODUCTIVE ORGANS

Stamens: (Androecium).

*Number.*—Average 8 to 10.

*Filament length.*—Approximately 0.7 cm.

*Filament color.*—Near RHS Red 49B.

*Anther length.*—0.1 cm.

*Anther color.*—Near RHS Yellow 1C.

*Anther shape.*—Round.

*Pollen color.*—Near RHS Yellow 5D.

*Pollen quantity.*—Scant.

Pistil: (Gynoecium).

*Number.*—Average 5.

*Length.*—Approximately 1.4 cm.

*Style color.*—Near White N155D, flushed Red 49A and Red-Purple 64A.

*Stigma.*—Shape: Linear. Color: Near RHS Red-Purple 64A. Ovary Color: Near RHS White 155B, flushed Red-Purple 64A.

OTHER CHARACTERISTICS

Fruits and seeds: Typical to Genus. Minute, less than 1 mm dry seeds. Colored between black and brown, too small to accurately measure with color chart.

Temperature tolerance: Tolerates temperatures from approximately −2° C. to at least 35° C.

Disease/pest resistance: More resistance to the "shattering" of Summer Stress Syndrome than other *Tacisedum* cultivars. Neither resistance or susceptibility to normal diseases and pests of *Tacisedum* has been observed.

Drought tolerance: Tolerates at least 3 weeks of high temperatures without supplemental water, showing no serious damage to plant.

What is claimed is:

1. A new and distinct cultivar of *Tacisedum* plant named 'SOLAR FLARE' as herein illustrated and described.

* * * * *